United States Patent [19]

Podszun et al.

[11] Patent Number: 5,733,957

[45] Date of Patent: Mar. 31, 1998

[54] FLAME RETARDANT POLYCARBONATE CONTAINING POLYCYCLIC PHOSPHORIC ACID ESTERS

[75] Inventors: Wolfgang Podszun, Köln; Thomas Eckel, Dormagen, both of Germany

[73] Assignee: Bayer AG, Leverkusen, Germany

[21] Appl. No.: 632,890

[22] Filed: Apr. 16, 1996

Related U.S. Application Data

[62] Division of Ser. No. 502,736, Jul. 11, 1995, abandoned.

[30] Foreign Application Priority Data

Jul. 22, 1994 [DE] Germany .................. 44 26 128.4

[51] Int. Cl.$^6$ ................................. C08K 5/523
[52] U.S. Cl. ................................. 524/127
[58] Field of Search ........................... 524/127, 126

[56] References Cited

U.S. PATENT DOCUMENTS

| 3,976,616 | 8/1976 | Combey et al. | 260/30.6 |
|---|---|---|---|
| 4,343,732 | 8/1982 | Zama et al. | 524/127 |
| 5,061,745 | 10/1991 | Wittman et al. | 524/139 |
| 5,204,394 | 4/1993 | Gosens et al. | 524/125 |
| 5,272,193 | 12/1993 | Fuhr et al. | 524/126 |
| 5,618,867 | 4/1997 | Bright et al. | 524/127 |

FOREIGN PATENT DOCUMENTS

| 286253 | 10/1988 | European Pat. Off. . |
|---|---|---|
| 345522 | 12/1989 | European Pat. Off. . |
| 363608 | 4/1990 | European Pat. Off. . |
| 406934 | 1/1991 | European Pat. Off. . |
| 428221 | 5/1991 | European Pat. Off. . |
| 2921325 | 12/1979 | Germany . |
| 49-31650 | 3/1974 | Japan . |
| 49-32939 | 3/1974 | Japan . |
| 49-40342 | 4/1974 | Japan . |
| 56-51492 | 5/1981 | Japan . |
| 57-55947 | 4/1982 | Japan . |
| 734766 | 8/1955 | United Kingdom . |
| 2061949 | 5/1981 | United Kingdom . |

OTHER PUBLICATIONS

CA 81: 121909 (Nov. 18, 1974).
CA 81: 121871 (Nov. 18, 1974).
CA 81: 136919 (Dec. 2, 1974).
CA 95: 186842 (Nov. 23, 1981).

*Primary Examiner*—Veronica P. Hoke
*Attorney, Agent, or Firm*—Connolly & Hutz

[57] ABSTRACT

The present invention relates to polycyclic phosphoric acid esters of the formula (I)

$$L-(O-\underset{\underset{O}{\|}}{\overset{\overset{Ar}{|}}{\underset{|}{O}}}{P}-O-Ar)_n \quad (I)$$

in which
L is an n-valent linear or branched aliphatic hydrocarbon residue with 2 to 30 C atoms, which may be OH-substituted and may contain up to 8 ether linkages,
Ar is an aryl residue or alkaryl residue and
n is 2 to 6,
to the use thereof as flame retardants in thermoplastics and to the thermoplastic moulding compounds.

20 Claims, No Drawings

FLAME RETARDANT POLYCARBONATE CONTAINING POLYCYCLIC PHOSPHORIC ACID ESTERS

CROSS-REFERENCE TO RELATED APPLICATION

The present application is a divisional application of U.S. patent application Ser. No. 08/502,736 filed on Jul. 11, 1995, in the names of Wolfgang Podszun et al, now abandoned.

The present invention relates to polycyclic phosphoric acid esters which are derived from phenols and aliphatic polyols, to the use thereof as flame retardants in thermoplastics and to the thermoplastic moulding compounds.

Aromatic phosphoric acid esters, such as for example triphenyl phosphate, are highly effective flame retardants for thermoplastics, such as for example polycarbonate. U.S. Pat. No. 5,061,745, for example, describes polymer blends prepared from aromatic polycarbonate, ABS graft polymer and/or copolymers containing styrene and monophosphates as flame retardant additives. A disadvantage of these monocyclic phosphoric acid esters is their good diffusibility and insufficiently low volatility, which may lead to undesirable migration of the flame retardant in the moulding.

DE-A 2 921 325 describes flame resistant polycarbonate compounds prepared from an aromatic polycarbonate and a phosphorus compound which is, for example, of the following formula:

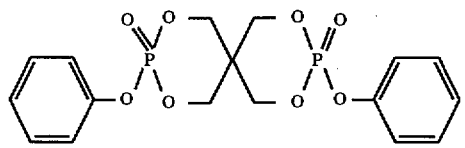

The migration capacity of this phosphorus compound is also, however, considerable.

U.S. Pat. No. 5,204,394 describes purely aromatic polycyclic phosphoric acid esters which may provide advantages as flame retardants in specific formulations.

The object of the present invention is to provide phosphoric acid esters with elevated flame retardant effect, low volatility, low migration tendency and good processing characteristics.

The present invention provides polycyclic phosphoric acid esters of the formula (I)

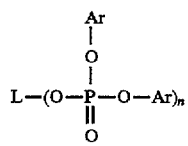

in which
L is an n-valent linear or branched aliphatic hydrocarbon residue with 2 to 30 C atoms, which may be OH-substituted and may contain up to 8 ether linkages,
Ar is an aryl residue or alkaryl residue and
n is 2 to 6.

Preferred polycyclic phosphoric acid esters are those in which
L is an n-valent aliphatic hydrocarbon residue with 3 to 15 C atoms, which may be OH-substituted and may contain up to 3 ether linkages, and
n is 2 to 6.

The following are, for example, particularly suitable hydrocarbon residues L:

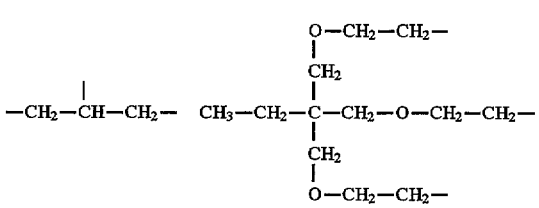

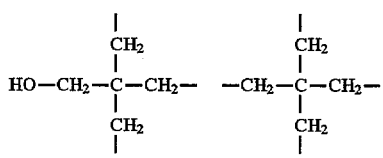

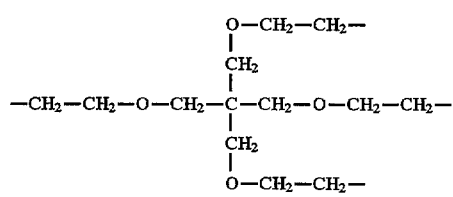

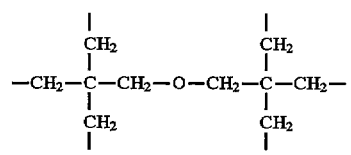

Ar in particular denotes phenyl, tolyl, xylenyl, p-octylphenyl, p-butylphenyl, naphthyl.

Ar particularly preferably denotes phenyl.

The following polycyclic phosphoric acid esters may be cited by way of example

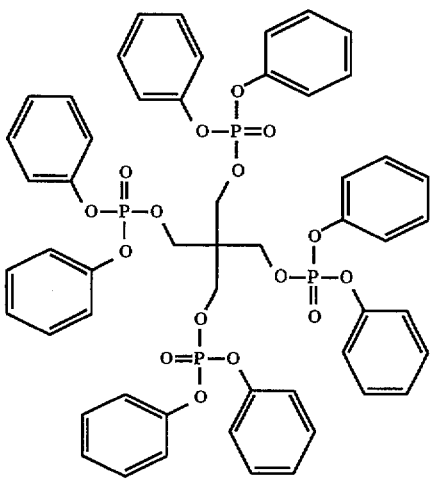

Formula (Ia)

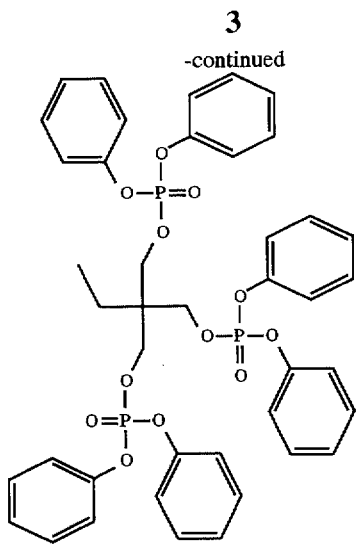

Formula (Ib)

The polycyclic phosphoric acid esters may be used both in pure form and as a mixture of relatively high and low molecular weight compounds.

The phosphoric acid esters according to the invention are conveniently synthesised in pure form by reacting diaryl chlorophosphate with the underlying aliphatic hydroxyalkyl compound in an absolute organic solvent in the presence of an acid scavenger. In general, the reaction is performed at temperatures of $-30°$ C. to $+70°$ C., preferably of $-10°$ C. to $+10°$ C. Examples of suitable solvents are chloroform, methylene chloride, tert.-butyl methyl ether and methyl ethyl ketone. Suitable acid scavengers are amines, for example dicyclohexylamine or triethylamine.

Instead of diaryl chlorophosphate, phosphorus oxychloride may be used as the starting material, initially reacting this with two mol of phenol and then, without further working up, performing the reaction with the aliphatic hydroxyalkyl compound.

In this case, the reaction product contains fractions of relatively high and low molecular weight compounds. The resultant product mixture is also highly suitable as a flame retardant.

The phosphoric acid esters according to the invention are suitable for imparting flame retardant properties to thermoplastics, in particular to polycarbonates and blends of polycarbonates with, for example, styrene polymers.

The quantity of phosphoric acid ester used is generally 0.5 to 20 wt. %, preferably 3 to 18 wt. %.

The manner in which the flame retardant is incorporated into the thermoplastic is non-critical, it may, for example, be achieved by melt compounding using a kneader or extruder or also in solution.

The present invention also provides thermoplastic moulding compounds containing

A) 40 to 98, preferably 60 to 97 parts by weight of aromatic polycarbonate, and one or more polymers selected from the group comprising the following components B) 3 to 50, preferably 5 to 40 parts by weight of vinyl copolymer prepared from B.1) 50 to 98, preferably 60 to 95 parts by weight of styrene, α-methylstyrene, ring-substituted styrenes, $C_1$–$C_8$ alkyl methacrylates, $C_1$–$C_8$ alkyl acrylates or mixtures thereof and B.2) 50 to 2, preferably 40 to 5 parts by weight of acrylonitrile, methacrylonitrile, $C_1$–$C_8$ alkyl methacrylates, $C_1$–$C_8$ alkyl acrylates, maleic anhydride, N-substituted maleimides and mixtures thereof, C) 0.5 to 40 parts by weight, preferably 1 to 20 parts by weight, particularly preferably 2 to 12 parts by weight of graft polymer, D) 0.5 to 20 parts by weight, preferably 1 to 18 parts by weight, particularly preferably 2 to 15 parts by weight of polycyclic phosphoric acid esters of the formula (I)

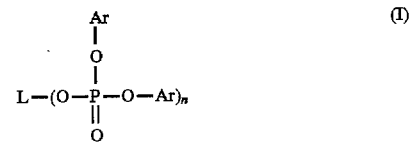

in which

L is an n-valent linear or branched aliphatic hydrocarbon residue with 2 to 30 C atoms, which may be OH-substituted and may contain up to 8 ether linkages, Ar is an aryl residue or alkaryl residue and n is 2 to 6, E) 0.05 to 5 parts by weight, preferably 0.1 to 1 part by weight, particular preferably 0.1 to 0.5 parts by weight of fluorinated polyolefin with an average particle diameter of 0.05 to 1,000 μm, a density of 1.2 to 2.3 g/cm³ and a fluorine content of 65 to 76 wt. %, F) 2 to 30, preferably 5 to 25 parts by weight of polyalkylene terephthalate.

The sum of all parts by weight A+B+C+D+E+F is 100.

In addition to polycarbonate and flame retardant, the thermoplastic moulding compound may thus contain copolymer and/or graft polymer according to C) and/or PTFE according to E) and/or polyalkylene terephthalate according to F).

Component A

Thermoplastic, aromatic polycarbonates according to component A which are suitable according to the invention are those based on diphenols of the formula (II)

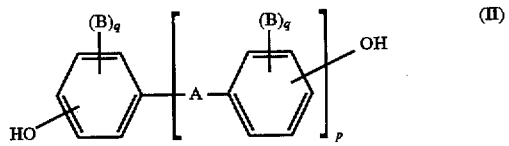

in which

A is a single bond, $C_1$–$C_5$ alkylene, $C_2$–$C_5$ alkylidene, $C_5$–$C_6$ cycloalkylidene, —S— or —$SO_2$—, B is chlorine or bromine q is 0, 1 or 2 and p is 1 or 0 or alkyl-substituted dihydroxyphenylcycloalkanes of the formula (III)

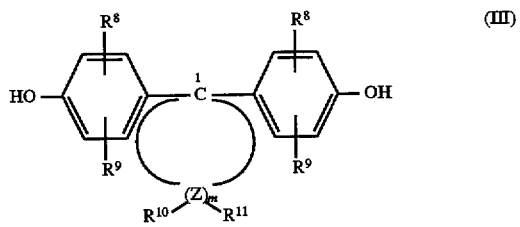

worin in which $R^8$ and $R^9$ mutually independently mean hydrogen, halogen, preferably chlorine or bromine, $C_1$–$C_8$ alkyl, $C_5$–$C_6$ cycloalkyl, $C_6$–$C_{10}$ aryl, preferably phenyl, and $C_7$–$C_{12}$ aralkyl, preferably phenyl-$C_1$–$C_4$-alkyl, in particular benzyl, m means an integer of 4, 5, 6 or 7, preferably 4 or 5, $R^{10}$ and $R^{11}$ mutually independently, individually selectably for each Z mean hydrogen or $C_1$–$C_6$ alkyl and Z means carbon, provided that on at least one atom Z, $R^{10}$ and $R^{11}$ simultaneously mean alkyl.

Suitable diphenols of the formula (II) are, for example, hydroquinone, resorcinol, 4,4'-dihydroxydiphenyl, 2,2-bis-(4-hydroxyphenyl)propane, 2,4-bis-(4-hydroxyphenyl)-2-methylbutane, 1,1-bis-(4-hydroxyphenyl)cyclohexane, 2,2-bis-(3-chloro-4-hydroxyphenyl)propane, 2,2-bis-(3,5-dibromo-4-hydroxyphenyl)propane.

Preferred diphenols of the formula (II) are 2,2-bis-(4-hydroxyphenyl)propane, 2,2-bis-(3,5-dichloro-4-hydroxyphenyl)propane and 1,1-bis-(4-hydroxyphenyl)-cyclohexane.

Preferred diphenols of the formula (III) are 1,1-bis-(4-hydroxyphenyl)-3,3-dimethylcyclohexane, 1,1-bis-(4-hydroxyphenyl)-3,3,5-trimethylcyclohexane and 1,1-bis-(4-hydroxyphenyl)-2,4,4-trimethylcyclopentane.

Polycarbonates which are suitable according to the invention are both homopolycarbonates and copolycarbonates.

Component A may also be a blend of the above-stated thermoplastic polycarbonates.

Polycarbonates may be produced in a known manner from diphenols with phosgene using the phase interface process or using the homogeneous phase process, the so-called pyridine process, wherein the molecular weight may be adjusted in a known manner with an appropriate quantity of known chain terminators.

Suitable chain terminators are, for example, phenol, p-chlorophenol, p-tert.-butylphenol or 2,4,6-tribromophenol, as well as long-chain alkylphenols, such as 4-(1,3-tetramethylbutyl)phenol according to DE-OS 2 842 005 or monoalkylphenol or dialkylphenol with a total of 8 to 20 C atoms in the alkyl substituents according to DE-OS 3 506 472, such as 3,5-di-tert.-butylphenol, p-isooctylphenol, p-tert.-octylphenol, p-dodecylphenol and 2-(3,5-dimethylheptyl)phenol and 4-(3,5-dimethylheptyl)phenol.

The quantity of chain terminators is generally between 0.5 and 10 mol. %, relative to the sum of the diphenols of the formulae (II) and/or (III) used in the particular case.

Polycarbonates A suitable according to the invention have average molecular weights ($M_w$, weight average, for example determined by ultracentrifugation or light-scattering) of 10,000 to 200,000, preferably of 20,000 to 80,000.

Polycarbonates A suitable according to the invention may be branched in a known manner, namely by the incorporation of 0.05 to 2 mol. %, relative to the total of diphenols used, of trifunctional or greater than trifunctional compounds, for example such compounds with three or more phenolic groups.

Preferred polycarbonates, apart from bisphenol A homopolycarbonate, are the copolycarbonates of bisphenol A with up to 15 mol. %, relative to the total of diphenols, of 2,2-bis-(3,5-dibromo-4-hydroxyphenyl)propane and the copolycarbonates of bisphenol A with up to 60 mol. %, relative to the molar total of diphenols, of 1,1-bis-(4-hydroxyphenyl)-3,3,5-trimethylcyclohexane.

The polycarbonates A may be partially or entirely replaced by aromatic polyester carbonates.

Component B

Vinyl copolymers according to component B which may be used according to the invention are those prepared from at least one monomer from the series: styrene, α-methylstyrene and/or ring-substituted styrenes, $C_1$–$C_8$ alkyl methacrylate, $C_1$–$C_8$ alkyl acrylate (B.1) with at least one monomer from the series: acrylonitrile, methacrylonitrile, $C_1$–$C_8$ alkyl methacrylate, $C_1$–$C_8$ alkyl acrylate, maleic anhydride and/or N-substituted maleimide (B.2).

$C_1$–$C_8$ alkyl acrylates and $C_1$–$C_8$ alkyl methacrylates are respectively esters of acrylic acid and methacrylic acid and monohydric alcohols with 1 to 8 C atoms. Methacrylic acid methyl ester, ethyl ester and propyl ester are particularly preferred. Methyl methacrylate is cited as a particularly preferred methacrylic acid ester.

Thermoplastic copolymers with a composition according to component B may be produced as a by-product of graft polymerisation to produce component C, particularly if large quantities of monomers are grafted onto small quantities of rubber. The quantity of copolymer B to be used according to the invention does not include these by-products of graft polymerisation.

The copolymers according to component B) are resinous thermoplastics which contain no rubber.

The thermoplastic copolymers B contain 50 to 98, preferably 60 to 95 parts by weight of B.1 and 50 to 2, preferably 40 to 5 wt. % of B.2.

Particularly preferred copolymers B are those prepared from styrene with acrylonitrile and optionally with methyl methacrylate, from α-methylstyrene with acrylonitrile and optionally with methyl methacrylate or from styrene and α-methylstyrene with acrylonitrile and optionally with methyl methacrylate.

The styrene/acrylonitrile copolymers according to component B are known and may be produced by free-radical polymerisation, in particular by emulsion, suspension, solution or bulk polymerisation. The copolymers according to component B preferably have molecular weights $M_w$ (weight average, determined by light scattering or sedimentation) of between 15,000 and 200,000.

Particularly preferred copolymers B according to the invention are also random copolymers prepared from styrene and maleic anhydride, which may be produced by continuous bulk or solvent polymerisation of the corresponding monomers with incomplete conversion.

The proportions of the two components in the random styrene/maleic anhydride copolymers which are suitable according to the invention may be varied within broad limits. The preferred maleic anhydride content is between 5 and 25 wt. %.

The molecular weights ($\overline{M}_n$, number average) of the random styrene/maleic anhydride copolymers according to component B which are suitable according to the invention may vary over a wide range. The range from 60,000 to 200,000 is preferred. The preferred intrinsic viscosity of these products is from 0.3 to 0.9 (measured in dimethylformamide at 25° C.; see in this connection Hoffmann, Krömer, Kuhn, Polymeranalytik I, Stuttgart 1977, page 316 et seq.).

Instead of styrene, the vinyl copolymers B may also contain ring-substituted styrenes, such as p-methylstyrene, vinyltoluene, 2,4-dimethylstyrene and other substituted styrene such as α-methylstyrene.

Component C

The graft polymers C) comprise, for example, graft copolymers with rubber-elastic properties which may substantially be obtained from at least two of the following monomers: chloroprene, 1,3-butadiene, isoprene, styrene, acrylonitrile, ethylene, propylene, vinyl acetate and (meth)

acrylic acid esters with 1 to 18 C atoms in the alcohol component; consequently polymers as are, for example, described in Methoden der Organischen Chemie (Houben-Weyl), volume 14/1, Georg Thieme Verlag, Stuttgart 1961, pages 393–406 and in C. B. Buckhall Toughened Plastics, Appl. Science Publishers, London 1977. Preferred polymers C) are partially crosslinked and have gel contents of above 20 wt. %, preferably of above 40 wt. %, in particular of above 60 wt. %.

Preferred graft polymers C) comprise graft polymers prepared from:

C.1) 5 to 95, preferably 30 to 80 parts by weight of a mixture of

C.1.1) 50 to 95 parts by weight of styrene, α-methylstyrene, halogen or methyl ring-substituted styrene, $C_1$–$C_8$ alkyl methacrylate, in particular methyl methacrylate, $C_1$–$C_8$ alkyl acrylate, in particular methyl acrylate, or mixtures of these compounds and C.1.2) 5 to 50 parts by weight of acrylonitrile, methacrylonitrile, $C_1$–$C_8$ alkyl methacrylates, in particular methyl methacrylate, $C_1$–$C_8$ alkyl acrylate, in particular methyl acrylate, maleic anhydride, $C_1$–$C_4$ alkyl or phenyl N-substituted maleimides or mixtures of these compounds onto C.2) 5 to 95, preferably 20 to 70 parts by weight of polymer with a glass transition temperature of below −10° C.

Preferred grafting backbones C2 are polybutadiene, butadiene/styrene copolymers and acrylate rubbers.

Preferred graft polymers C) are, for example, polybutadienes, butadiene/styrene copolymers and acrylate rubbers grafted with styrene and/or acrylonitrile and/or (meth)acrylic acid alkyl esters; i.e. copolymers of the type described in DE-OS 1 694 173 (=U.S. Pat. No. 3,564,077); polybutadienes, butadiene/styrene or butadiene/acrylonitrile copolymers, polyisobutenes or polyisoprenes grafted with acrylic or methacrylic acid esters, vinyl acetate, acrylonitrile, styrene and/or alkylstyrenes, as are, for example, described in DE-OS 2 348 377 (=U.S. Pat. No. 3,919,353).

Particularly preferred polymers C) are, for example, ABS polymers, as are, for example, described in DE-OS 2 035 390 (=U.S. Pat. No. 3,644,574) or in DE-OS 2 248 242 (=GB-PS 1,409,275).

Preferred graft polymers C) are furthermore graft polymers which may be obtained by graft reaction of I. 10 to 70, preferably 15 to 50, in particular 20 to 40 wt. %, relative to the graft product, of at least one (meth) acrylic acid ester or 10 to 70, preferably 15 to 50, in particular 20 to 40 wt. % or a mixture of 10 to 50, preferably 20 to 35 wt. %, relative to the mixture, of acrylonitrile or (meth)acrylic acid ester and 50 to 90, preferably 65 to 80 wt. %, relative to the mixture, of styrene onto II. 30 to 90, preferably 50 to 85, in particular 60 to 80 wt. %, relative to the graft product, of a butadiene polymer having at least 50 wt. %, relative to II, of butadiene residues as the grafting backbone, wherein the gel content of the grafting backbone II is preferably at least 70 wt. % (measured in toluene), the degree of grafting G is 0.15 to 0.55 and the average particle diameter $d_{50}$ of the graft polymer C) is 0.05 to 2, preferably 0.1 to 0.6 μm.

(Meth)acrylic acid esters I are esters of acrylic acid or methacrylic acid and monohydric alcohols with 1 to 18 C atoms. Methacrylic acid methyl ester, ethyl ester and propyl ester are particularly preferred.

In addition to butadiene residues, the grafting backbone II may contain up to 50 wt. %, relative to II, of residues of other ethylenically unsaturated monomers, such as styrene, acrylonitrile, esters of acrylic or methacrylic acid with 1 to 4 C atoms in the alcohol component (such as methyl acrylate, ethyl acrylate, methyl methacrylate, ethyl methacrylate), vinyl esters and/or vinyl ethers. The preferred grafting backbone II consists of pure polybutadiene.

Since, as is known, the graft monomers are not necessarily entirely grafted onto the grafting backbone during the graft reaction, graft polymers C) according to the invention are also taken to mean those products obtained by polymerisation of the graft monomers in the presence of the grafting backbone.

The degree of grafting G describes the ratio of the weight of grafted graft monomers to the weight of the grafting backbone and is dimensionless.

The average particle size $d_{50}$ is the diameter both above and below which are found 50 wt. % of the particles. This diameter may be determined by ultracentrifuge measurements (W. Scholtan, H. Lange, Kolloid Z. & Z. Polymere 250 (1972), 782–796).

Particularly preferred graft polymers C) are, for example, also graft polymers prepared from (a) 20 to 90 wt. %, relative to C) of acrylate rubber with a glass transition temperature of below −20° C. as the grafting backbone and (b) 10 to 80 wt. %, relative to C), of at least one polymerisable, ethylenically unsaturated monomer, the homo- or copolymers of which, in the absence of a), would have a glass transition temperature of above 25° C., as the grafting monomers.

The acrylate rubbers (a) of the polymers C) are preferably polymers prepared from acrylic acid esters, optionally with up to 40 wt. %, relative to (a), of other polymerisable, ethylenically unsaturated monomers. Preferred polymerisable acrylic acid esters include $C_1$–$C_8$ alkyl esters, for example methyl, ethyl, n-butyl, n-octyl and 2-ethylhexyl ester; halogenoalkyl esters, preferably halogeno-$C_1$–$C_8$-alkyl esters, such as chloroethyl acrylate, together with mixtures of these monomers.

Monomers with more than one polymerisable double bond may be copolymerised for crosslinking purposes. Preferred examples of crosslinking monomers are esters of unsaturated monocarboxylic acids with 3 to 8 C atoms and unsaturated monohydric alcohols with 3 to 12 C atoms or saturated polyols with 2 to 4 OH groups and 2 to 20 C atoms, such as for example ethylene glycol dimethacrylate, allyl methacrylate; polyunsaturated heterocyclic compounds, such as for example trivinyl and triallyl cyanurate; polyfunctional vinyl compounds, such as di- and trivinyl benzenes; as well as triallyl phosphate and diallyl phthalate.

Preferred crosslinking monomers are allyl methacrylate, ethylene glycol dimethacrylate, diallyl phthalate and heterocyclic compounds having at least three ethylenically unsaturated groups.

Particularly preferred crosslinking monomers are the cyclic monomers triallyl cyanurate, triallyl isocyanurate, trivinyl cyanurate, triacryloyl hexahydro-s-triazine, triallyl benzenes.

The quantity of the crosslinking monomers is preferably 0.02 to 5, in particular 0.05 to 2 wt. %, relative to the grafting backbone (a).

In the case of cyclic crosslinking monomers with at least three ethylenically unsaturated groups, it is advantageous to restrict the quantity to below 1 wt. % of the grafting backbone (a).

Preferred "other" polymerisable, ethylenically unsaturated monomers which may optionally be used in addition to the acrylic acid alkyl esters for production of the grafting backbone (a) are, for example, acrylonitrile, styrene, α-methylstyrene, acrylamides, vinyl $C_1$–$C_6$ alkyl ethers, methyl methacrylate, butadiene. Preferred acrylate rubbers as the grafting backbone (a) are emulsion polymers having a gel content of at least 60 wt. %.

Further suitable grafting backbones are silicone rubbers with active grafting sites, as are described in DE-OS 37 04 657, DE-OS 37 04 655, DE-OS 36 31 540 and DE-OS 36 31 539.

The gel content of the grafting backbone (a) is measured in dimethylformamide at 25° C. (M. Hoffmann, H. Krömer, R. Kuhn, Polymeranalytik I & II, Georg Thieme Verlag, Stuttgart 1977).

The aqueous dispersions of graft polymer C) to be used for the preferred embodiment of co-precipitation with the tetrafluoroethylene polymer E) generally have solids contents of 25 to 60, preferably of 30 to 40 wt. %.

Component D

The polycyclic phosphoric acid esters mentioned and described above are used as the flame retardant.

Component E

The fluorinated polyolefins E) are high molecular weight compounds and have glass transition temperatures of above –30° C., generally of above 100° C., fluorine contents preferably of 6 to 76, in particular of 70 to 76 wt. %, average particle diameters d50 of 0.05 to 1,000, preferably of 0.08 to 20 µm. In general, the fluorinated polyolefins E) have a density of 1.2 to 2.3 g/cm$^3$. Preferred fluorinated polyolefins E) are polytetrafluoroethylene, polyvinylidene-fluoride, tetrafluoroethylene/hexafluoropropylene and ethylene/tetrafluoroethylene copolymers. The fluorinated polyolefins are known (c.f. Vinyl and Related Polymers by Schildknecht, John Wiley & Sons Inc., New York, 1962, pages 484–494; Fluoropolymers by Wall, Wiley-Interscience, John Wiley & Sons Inc., New York, volume 13, pages 623–654; Modern Plastics Encyclopedia, 1970–1971, volume 47, n° 10A, October 1970, McGraw-Hill Inc., New York, pages 134 and 774; Modern Plastics Encyclopedia, 1975–1976, October 1975, volume 52, n° 10A, McGraw-Hill Inc., New York, pages 27, 28 and 472 and U.S. Pat. Nos. 3,671,487, 3,723,373 and 3,838,092).

They may be produced using known process, thus for example by polymerisation of tetrafluoroethylene in an aqueous medium with a free-radical forming catalyst, for example sodium, potassium or ammonium peroxydisulphate at pressures of 7 to 71 kg/cm$^2$ and at temperatures of 0° to 200° C., preferably at temperatures of 20° to 100° C. (See, for example, U.S. Pat. No. 2,393,967 for further details). Depending upon the form in which they are used, the density of these materials may be between 1.2 and 2.3 g/cm$^3$ and the average particle size between 0.05 and 1,000 µm.

Fluorinated polyolefins E) which are preferred according to the invention are tetrafluoroethylene polymers having average particle diameters of 0.5 to 20 µm, preferably of 0.08 to 10 µm, and a density of 1.2 to 1.9 g/cm$^3$ and are preferably used in the form of a coagulated mixture of emulsions of the tetrafluoroethylene polymers E) with emulsions of the graft polymers C).

Suitable fluorinated polyolefins E) which may be used in powder form are tetrafluoroethylene polymers with average particle diameters of 100 to 1,000 µm and densities of 2.0 g/cm$^3$ to 2.3 g/cm$^3$.

A coagulated mixture of C) and E) is produced by first mixing an aqueous emulsion (latex) of a graft polymer C) having an average particle diameter of 0.05 to 2 µm, in particular of 0.1 to 0.6 µm, with a finely divided emulsion of a tetrafluoroethylene polymer E) in water having an average particle diameter of 0.05 to 20 µm, in particular of 0.08 to 10 µm; suitable tetrafluoroethylene polymer emulsions customarily have solids contents of 30 to 70 wt. %, in particular of 50 to 60 wt. %. The emulsions of the graft polymers C) have solids contents of 25 to 50 wt. %, preferably of 30 to 45 wt. %.

The quantity stated in the description of component C includes the proportion of the graft polymer in the coagulated mixture of graft polymer and fluorinated polyolefins.

The weight ratio of graft polymer C) to tetrafluoroethylene polymer E) in the emulsion mixture is 95:5 to 60:40. The emulsion mixture is then coagulated in a known manner, for example by spray drying, freeze drying or coagulation by adding inorganic or organic salts, acids, bases or organic, water-miscible solvents, such as alcohols, ketones, preferably at temperatures of 20° to 150° C., in particular of 50° to 100° C. If necessary, drying may be performed at 50° to 200° C., preferably at 70° to 100° C.

Suitable tetrafluoroethylene polymer emulsions are customary commercial products and are offered for sale, or example by DuPont, as Teflon® 30 N.

Component F

For the purposes of the invention, polyalkylene terephthalates are reaction products of aromatic dicarboxylic acids or the reactive derivatives thereof (for example dimethyl esters or anhydrides) and aliphatic, cycloaliphatic or araliphatic diols and mixtures of these reaction products.

Preferred polyalkylene terephthalates may be produced from terephthalic acid (or the reactive derivatives thereof) and aliphatic or cycloaliphatic diols with 2 to 10 C atoms using known methods (Kunststoff-Handbuch, volume VIII, pages 695 et seq., Karl Hanser Verlag, Munich 1973).

Preferred polyalkylene terephthalates contain at least 80, preferably 90 mol. %, relative to the dicarboxylic acid component, of terephthalic acid residues and at least 80, preferably 90 mol. %, relative to the diol component, of ethylene glycol and/or 1,4-butanediol residues.

In addition to terephthalic acid residues, the preferred polyalkylene terephthalates may contain up to 20 mol. % of residues of aromatic dicarboxylic acids with 8 to 14 C atoms or aliphatic dicarboxylic acids with 4 to 12 C atoms, such as residues of phthalic acid, isophthalic acid, 2,6-naphthalenedicarboxylic acid, 4,4'-diphenyldicarboxylic acid, succinic, adipic, sebacic, azelaic, cyclohexanediacetic acid.

In addition to ethylene glycol or 1,4-butanediol residues, the preferred polyalkylene terephthalates may contain up to 20 mol. % of other aliphatic diols with 3 to 12 atoms or cycloaliphatic diols with 6 to 21 C atoms, for example residues of 1,3-propanediol, 2-ethylene-1,3-propanediol, neopentyl glycol, 1,5-pentanediol, 1,6-hexanediol, 1,4-cyclohexanedimethanol, 3-methyl-2,4-pentanediol, -methyl-2,4-pentanediol, 2,2,4-trimethyl-1,3-pentanediol and 1,6,2-ethyl-1,3-hexanediol, 2,2-diethyl-1,3-propanediol, 2,5-hexanediol, 1,4-di-(β-hydroxyethoxy)-benzene, 2,2-bis-(3-β-hydroxyethoxyphenyl)propane and 2,2-bis-(4-hydroxypropoxyphenyl)propane (DE-OS 24 07 674, 24 07 776, 27 15 932).

The polyalkylene terephthalates may be branched by incorporating relatively small quantities of tri- or tetrahydric alcohols or tri- or tetrabasic carboxylic acids, as are, for example, described in DE-OS 1 900 270 and U.S. Pat. No. 3,692,744. Examples of preferred branching agents are trimesic acid, trimellitic acid, trimethylolethane and trimethylolpropane and pentaerythritol.

It is advisable to use no more than 1 mol. % of the branching agent relative to the acid component.

Particularly preferred polyalkylene terephthalates are those produced solely from terephthalic acid and the reactive derivatives thereof (for example dialkyl esters) and ethylene glycol and/or 1,4-butanediol (polyethylene and polybutylene terephthalate), together with blends of these polyalkylene terephthalates.

Preferred polyalkylene terephthalates are also copolyesters produced from at least two of the above-stated acid components and/or from at least two of the above-stated alcohol components, particularly preferred copolyesters are poly(ethylene glycol/1,4-butanediol) terephthalates.

The polyalkylene terephthalates preferably used as component F generally have an intrinsic viscosity of approximately 0.5 to 1.5 dl/g, preferably of 0.5 to 1.3 dl/g, in each case measured in phenol/o-dichlorobenzene (1:1 parts by weight) at 25° C.

The individual components A), B), C), D), E) or F) may each also be used as a mixture.

The moulding compounds according to the invention may contain customary additives, such as lubricants and mould release agents, nucleating agents, antistatic agents, stabilisers, fillers and reinforcing materials, together with dyes and pigments.

Filled or reinforced moulding compounds may contain up to 60, preferably 10 to 40 wt. %, relative to the filled or reinforced moulding compound, of fillers and/or reinforcing materials. Preferred reinforcing materials are glass fibres. Preferred fillers, which may also have a reinforcing action, are glass beads, mica, silicates, quartz, talcum, titanium dioxide, wollastonite.

The moulding compounds according to the invention consisting of components A to F and optionally further additives such as stabilisers, dyes, pigments, lubricants and mould release agents, fillers and reinforcing materials, nucleating agents and antistatic agents are produced by mixing the individual constituents in a known manner and melt-compounding or melt-extruding them at temperatures of 200° C. to 330° C. in customary equipment, such as internal kneaders, extruders and twin screw extruders, wherein component E) is preferably used in the form of the above-mentioned coagulated mixture.

The present invention thus also provides a process for the production of thermoplastic moulding compounds consisting of components A to F optionally together with stabilisers, dyes, pigments, lubricants and mould release agents, fillers and reinforcing materials, nucleating agents and antistatic agents, which process is characterised in that, once mixed at 200° to 330° C., components A to F optionally together with stabilisers, dyes, pigments, lubricants and mould release agents, fillers and reinforcing materials, nucleating agents and/or antistatic agents are melt-compounded or melt-extruded in customary equipment, wherein component F is preferably used in the form of a coagulated mixture with component C.

The individual constituents may be mixed in a known manner both successively and simultaneously and indeed both at approximately 20° C. (room temperature) and at a higher temperature.

The moulding compounds of the present invention may be used to produce mouldings of any kind. Mouldings may in particular be produced by injection moulding. Examples of mouldings which may be produced are: casing components of any kind, for example for household equipment, such as juice extractors, coffee machines, mixers, for office equipment or covers for the construction sector and components for the automotive sector. They are also used in the electrical engineering sector because they have very good electrical properties.

The moulding compounds are particularly suitable for the production of thin-walled mouldings (for example data processing equipment casing components), where requirements for notched impact strength and stress cracking resistance are particularly severe.

Another manner of processing is the production of mouldings by thermoforming from previously produced sheets or films.

EXAMPLES

Example 1

Synthesis of the phosphoric acid ester according to formula (Ia)

3.40 g of pentaerythritol and 12.12 g of triethylamine dissolved in 150 ml of absolute tert.-butyl methyl ketone are introduced into a stirred apparatus with exclusion of moisture. 26.86 g of diphenyl chlorophosphate are added dropwise within 90 minutes, wherein sufficient cooling is provided to maintain the reaction temperature at 0° to 1° C. After the addition, the mixture is stirred for a further 10 hours at room temperature. The resultant precipitate is filtered out, the organic solution is washed repeatedly with water and dried with sodium sulphate. After evaporation of the solvent, 25.76 g of a colourless solid are obtained.
Elemental analysis:

|            | C     | H    | P     |
|------------|-------|------|-------|
| calculated | 59.78 | 4.54 | 11.63 |
| found      | 59.72 | 4.61 | 11.48 |

Example 2

Synthesis of the phosphoric acid ester according to formula (Ib)

4.42 g of trimethylolpropane and 12.12 g of triethylamine dissolved in 150 ml of absolute tert.-butyl methyl ketone are introduced into a stirred apparatus with exclusion of moisture. 26.86 g of diphenyl chlorophosphate are added dropwise within 90 minutes, wherein sufficient cooling is provided to maintain the reaction temperature at 0° to 1° C. After the addition, the mixture is stirred for a further 10 hours at room temperature. The resultant precipitate is filtered out, the organic solution is washed repeatedly with water and dried with sodium sulphate. After evaporation of the solvent, 26.16 g of a colourless solid are obtained.
Elemental analysis:

|            | C     | H    | P     |
|------------|-------|------|-------|
| calculated | 60.73 | 4.97 | 11.19 |
| found      | 60.82 | 5.04 | 11.03 |

Applicational testing

Component A

Bisphenol A based polycarbonate with a relative solution viscosity of 1.26 to 1.28 measured in methylene chloride at 25° C. and a concentration of 0.5 g/100 ml.

Component B

Styrene/acrylonitrile copolymer with a styrene/acrylonitrile ratio of 72:28 and an intrinsic viscosity of 55 dl/g (measured in dimethylformamide at 20° C.).

Component C

Graft polymer of 45 parts by weight of styrene and acrylonitrile in a 72:28 ratio onto 55 parts by weight of particulate crosslinked polybutadiene rubber (average particle diameter $d_{50}$=0.4 μm) produced by emulsion polymerisation.

Component D

Phosphorus compound according to formula (Ia).

Component E

Tetrafluoroethylene polymer as a coagulated mixture prepared from a SAN graft polymer emulsion according to C) in water and a tetrafluoroethylene polymer emulsion in water. The weight ratio of graft polymer C) to the tetrafluoroethylene polymer D) in the mixture is 90 wt. % to 10 wt. %. The tetrafluoroethylene polymer emulsion has a solids content of 60 wt. %, the average particle diameter is between 0.05 and 0.5 μm. The SAN graft polymer emulsion has a solids content of 34 wt. % and an average latex particle diameter ($d_{50}$) of 0.4 μm.

Production of component E

The emulsion of the tetrafluoroethylene polymer (Teflon 30 N from DuPont) is mixed with the emulsion of the SAN graft polymer C) and stabilised with 1.8 wt. %, relative to polymer solids, of phenolic antioxidants. At 85° to 95° C., the mixture is coagulated with an aqueous solution of $MgSO_4$ (Epsom salts) and acetic acid at pH 4 to 5, filtered and washed until virtually free of electrolytes and then centrifuged to remove the majority of the water and thereafter dried at 100° C. to yield a powder. This powder may then be compounded with the other components in the stated equipment.

Production of test specimens

The blends stated in table 1 are produced in a 3 liter internal kneader. Test specimens of dimensions of 127× 12.7×1.6 mm are injection moulded at 260° C. using an Arburg 270 E injection moulding machine.

TABLE 1

Composition (stated in parts by weight)

| Example | A | B | C | E | D compound of the formula (Ia) |
|---|---|---|---|---|---|
| 3.1 | 67 | 10 | 7.5 | 3.5 | 11.5 |
| 3.2 | 67 | 10 | 7.5 | 3.5 | 12.5 |
| 3.3 | 67 | 10 | 7.5 | 3.5 | 13.5 |
| 3.4 | 67 | 10 | 7.5 | 3.5 | 14.5 |
| 3.5 | 67 | 10 | 7.5 | 3.5 | 15.5 |
| 3.6 | 67 | 10 | 7.5 | 3.5 | 16.5 |

Testing of fire behaviour

The test specimens are arranged vertically in such a manner that the underside of the test specimen is 305 mm above a strip of cotton dressing. Each test specimen is exposed to a flame for 10 seconds. Ignition is performed using a bunsen burner with a 10 mm high blue flame of methane. After removal of the ignition source, the time burning continues is measured and the tendency to drip assessed. Five test specimens are used for each test and the burning times averaged.

| | Fire behaviour | |
|---|---|---|
| Example | Average duration of burning [s] | Burning droplets |
| 3.1 | 25.0 | no |
| 3.2 | 7.6 | no |
| 3.3 | 4.0 | no |
| 3.4 | 3.5 | no |
| 3.5 | 2.5 | no |
| 3.6 | 1.3 | no |

We claim:

1. Thermoplastic moulding compound comprising

A) 40 to 98 parts by weight of aromatic polycarbonate,

B) 3 to 50 parts by weight of vinyl copolymer prepared from

B.1) 50 to 98 parts by weight of styrene, α-methylstyrene, ring-substituted styrenes, $C_1$–$C_8$ alkyl methacrylates, $C_1$–$C_8$ alkyl acrylates or mixtures thereof and B.2) 50 to 2 parts by weight of acrylonitrile, methacrylonitrile, $C_1$–$C_8$ alkyl methacrylates, $C_1$–$C_8$ alkyl acrylates, maleic anhydride, N-substituted maleimides and mixtures thereof, C) 0.5 to 40 parts by weight of graft polymer, D) 0.5 to 20 parts by weight of polycyclic phosphoric acid esters of the formula (I)

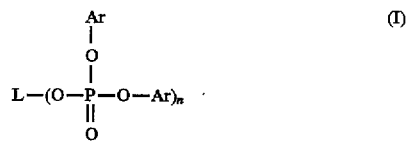

in which

L is an n-valent linear or branched aliphatic hydrocarbon residue with 2 to 30 C atoms, which may be OH-substituted and may contain up to 8 ether linkages, Ar is an aryl residue or alkaryl residue and n is 2 to 6, and E) 0.05 to 5 parts by weight of fluorinated polyolefin with an average particle diameter of 0.05 to 100 μm, a density of 1.2 to 2.3 g/cm$^3$ and a fluorine content of 65 to 76 wt. %.

2. Thermoplastic moulding compounds according to claim 1 containing additives selected from the group comprising stabilisers, dyes, pigments, lubricants and mould release agents, nucleating agents, antistatic agents, fillers and reinforcing materials.

3. Mouldings produced from thermoplastic moulding compounds according to claim 1.

4. Mouldings produced from thermoplastic moulding compounds according to claim 2.

5. Thermoplastic moulding compound consisting of

A) 40 to 98 parts by weight of aromatic polycarbonate,

B) 3 to 50 parts by weight of vinyl copolymer prepared from

B.1) 50 to 98 parts by weight of styrene, α-methylstyrene, ring-substituted styrenes, $C_1$–$C_8$ alkyl methacrylates, $C_1$–$C_8$ alkyl acrylates or mixtures thereof and B.2) 50 to 2 parts by weight of acrylonitrile, methacrylonitrile, $C_1$–$C_8$ alkyl methacrylates, $C_1$–$C_8$ alkyl acrylates, maleic anhydride, N-substituted maleimides and mixtures thereof, C) 0.5 to 40 parts by weight of graft polymer, D) 0.5 to 20 parts by weight of polycyclic phosphoric acid esters of the formula (I)

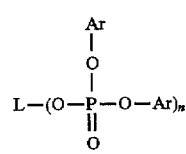

in which

L is an n-valent linear or branched aliphatic hydrocarbon residue with 2 to 30 C atoms, which may be OH-substituted and may contain up to 8 ether linkages, Ar is an aryl residue or alkaryl residue and n is 2 to 6, and E) 0.05 to 5 parts by weight of fluorinated polyolefin with an average particle diameter of 0.05 to 100 μm, a density of 1.2 to 2.3 g/cm³ and a fluorine content of 65 to 76 wt. %.

6. Thermoplastic moulding compound according to claim 5, wherein component D) is present in an amount of 12.5 to 20 parts by weight.

7. Thermoplastic moulding compound according to claim 5, wherein component D) is present in an amount of 13.5 to 20 parts by weight.

8. Thermoplastic moulding compound according to claim 5, wherein component D) is present in an amount of 14.5 to 20 parts by weight.

9. Thermoplastic moulding compound according to claim 5, wherein component D) is present in an amount of 15.5 to 20 parts by weight.

10. Thermoplastic moulding compound according to claim 5, wherein component D) is present in an amount of 16.5 to 20 parts by weight.

11. Thermoplastic moulding compound according to claim 5, wherein component D) is present in an amount of 12.5 to 16.5 parts by weight.

12. Thermoplastic moulding compound according to claim 1, wherein component D) is a phosphoric acid ester having the formula (Ia)

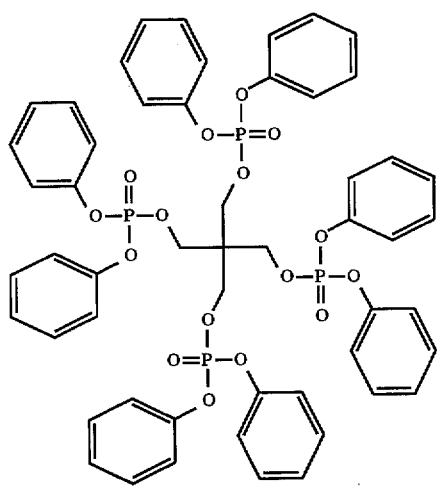

Formula (Ia)

13. Thermoplastic moulding compound according to claim 5, wherein component D) is a phosphoric acid ester having the formula (Ia)

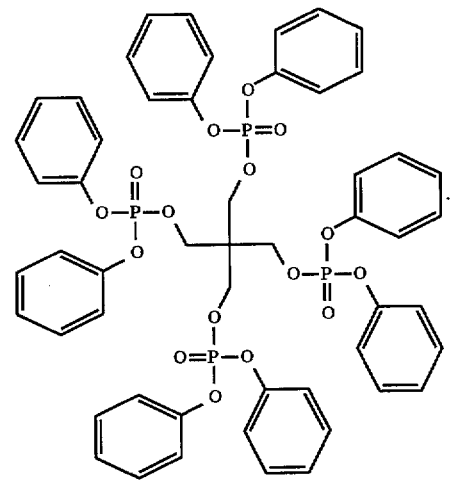

Formula (Ia)

14. Thermoplastic moulding compound according to claim 13, wherein said component D) is present in an amount of 12.5 to 20 parts by weight.

15. Thermoplastic moulding compound according to claim 13, wherein said component D) is present in an amount of 13.5 to 20 parts by weight.

16. Thermoplastic moulding compound according to claim 13, wherein said component D) is present in an amount of 14.5 to 20 parts by weight.

17. Thermoplastic moulding compound according to claim 13, wherein said component D) is present in an amount of 15.5 to 20 parts by weight.

18. Thermoplastic moulding compound according to claim 13, wherein said component D) is present in an amount of 16.5 to 20 parts by weight.

19. Thermoplastic moulding compound according to claim 13, wherein said component D) is present in an amount of 11.5 to 16.5 parts by weight.

20. Thermoplastic moulding compound according to claim 13, wherein said component D) is present in an amount of 12.5 to 16.5 parts by weight.

* * * * *